United States Patent [19]

Blauch et al.

[11] Patent Number: 5,253,719
[45] Date of Patent: Oct. 19, 1993

[54] PROCESS FOR DIAGNOSING FORMATION DAMAGE MECHANISM THROUGH THE USE OF RADIALLY ORIENTED CORE SAMPLES CUT FROM THE WELLBORE WALL

[75] Inventors: Matthew E. Blauch, Duncan; Milton B. Enderlin, Bartlesville, both of Okla.

[73] Assignee: Halliburton Company, Duncan, Okla.

[21] Appl. No.: 898,994

[22] Filed: Jun. 15, 1992

[51] Int. Cl.⁵ .................... E21B 25/00; E21B 49/06
[52] U.S. Cl. ..................................... 175/50; 175/20; 175/58; 73/153; 250/255
[58] Field of Search ................... 166/250, 255; 175/20, 175/58, 226; 73/864.44, 151, 153

[56] References Cited

U.S. PATENT DOCUMENTS

| | | |
|---|---|---|
| 4,280,568 | 7/1981 | McPhee et al. ............... 175/20 X |
| 5,105,894 | 4/1992 | Enderlin ...................... 166/255 X |
| 5,109,697 | 5/1992 | Millheim et al. ............. 175/50 X |

OTHER PUBLICATIONS

Gatlin, "Petroleum Engineering Drilling and Well Completions", Prentice-Hall, Inc., N.J., 1960, pp. 168, 169, 171, 172, 173, 184, 190, 191.

*Primary Examiner*—Stephen J. Novosad
*Attorney, Agent, or Firm*—Robert A. Kent; Keith Rutherford

[57] ABSTRACT

This invention provides a method for diagnosing formation damage mechanisms through the use of radially oriented core samples cut from the wellbore wall. Core samples are taken from the wellbore and analyzed under a number of different analytical methods. From the analysis of the cores the operator should be able to determine the type, extent, and severity of the formation damage, as well as the distance that damage extends out into the formation.

19 Claims, 1 Drawing Sheet

PROCESS FOR DIAGNOSING FORMATION DAMAGE MECHANISM THROUGH THE USE OF RADIALLY ORIENTED CORE SAMPLES CUT FROM THE WELLBORE WALL

BACKGROUND OF THE INVENTION

The present invention relates generally to a method for diagnosing the mechanisms of formation damage in both producing and injection wellbores, and more particularly, to a method for using radially oriented core samples cut from the wellbore wall to diagnose formation damage mechanisms in the wellbores.

Diagnosing formation damage mechanisms in both producing and injecting wells has long been a necessary activity. One of the common ways formation damage mechanisms have been diagnosed in the past is through sampling of scale, sludge, or build-up on production equipment contained in the wellbore, in surface equipment, and/or on tools used in work-over procedures. Samples of the scale, sludge, or build-up can be chemically analyzed to determine what the scale is and what would effectively treat that build-up.

There are some obvious drawbacks to the process utilizing an analysis of the scale. The first drawback is that this method only determines what scale or build-up occurs within the wellbore itself. While this may be an indication of formation damage, it is not a direct measurement of the actual damage mechanisms which are reducing the permeability and porosity of the formation itself. In addition, even if the formation itself is being plugged by scale, build-up, or sludge, there may not be evidence of that build-up anywhere within the wellbore itself or in any of the surface equipment.

Another method of determining formation damage mechanism is to use empirical data gathered from production or injection rates on a particular well or in a given field or reservoir in conjunction with results of past work-over treatments. This method can be used either alone or in conjunction with the analysis of gathered samples mentioned above. In this well-known method, the operator will track either the production or injection rate and look for a significant drop-off in either to indicate that formation damage has occurred. The operator will look for some significant change from the general decline expected in a production well or the constant injection pressures expected in an injection well. For injection wells, the indication of damage may also show up on a pressure versus barrels injected chart as a significant increase in the pressure necessary to inject the same total volume of fluid. Once the operator is alerted to the build-up of damage, he can then review past jobs done either on the particular well or on similar wells in the field to determine what jobs are particularly successful in cleaning up the formation damage. Once again, the method of empirical review has substantial drawbacks. First it is an indirect method of determining formation damage rather than a direct method. Secondly, the assumed basic rate of decline of the given well may actually have incorporated within it some gradual damage build-up that is causing a steeper rate of decline than would occur had there been no damage build-up. Using the empirical method merely attempts to get the well back to the basic rate of decline. Therefore, the use of the empirical method may be leaving a gradual build-up of damage in the well which is not being treated effectively by the methods which have proven to be successful to treat the damage mechanism causing the rapid build-up of formation damage.

Another conventional method of determining what types of formation damage may be occurring is to test well fluids and fluids that have been or will be injected into the wells. One way this is accomplished is to take fluid which is produced from a producing well and mix it with water which is injected in the same reservoir either through injection wells or through well treatments and determine if any precipitate forms when the two fluids are mixed together. If, for example, gypsum scale forms when the two waters are mixed together that is an indication that in the formation gypsum scale may be forming and causing damage.

Another way to use fluid tests is to evaluate the oil which is produced to determine its wax content and its tendency to form paraffin waxes. In addition, the oil may be tested to determine if it has a substantial number of low-end hydrocarbons which may cause a precipitation of a sludge or tar-like substance in the formation.

Once again, the analysis of formation fluids has serious drawbacks in that first, formation conditions can never be truly simulated to determine the actual mixture of the chemicals. Second, the chemicals are not in contact with the free ions that may be released by the formation rock itself. Thirdly, this analysis does not take into account injection of different fluids or chemicals in the past which may have caused formation damage which still exists in the formation. For example, fresh water may have been used in the past, whereas under the current practice of the operator no fresh water ever touches the formation. Finally, this type of analysis does not give any indication of whether there is a mud or filter cake build-up at the formation face nor does it show whether there is a build-up of fines in the formation in the near wellbore region. Once again, this method is merely a projection of what hypothetically might be occurring down in the formation itself.

One particular failing of all the methods mentioned above is that they provide no indication of how deep the formation damage extends out from the wellbore into the formation. Some formation damage may only exist within two inches or less from the wellbore whereas some may extend for up to a foot or more. The extent of the damage would greatly affect the design of a treatment which was directed at correcting that formation damage.

A method that can be used to determine the depth of the formation damage out into the reservoir is a pressure build up test. The pressure build up test is performed by shutting the well in for a number of days or even weeks. The wellbore pressure is then recorded using a pressure bomb and charted against time after shut-in. From the pressure versus time graph a skin factor may be calculated. The skin factor then may be used to calculate the permeability of the damaged zone and the depth which the damaged zone extends out into the formation. The pressure build-up method provides no direct information as to the cause of the formation damage. All that is gained is information concerning the severity and depth of the damage. This method can be very expensive because production or injection must cease completely over the entire testing period. A determination of formation damage by the skin factor method can result in erroneous results. The determined skin factor does not differentiate between a positive skin due to formation damage and other factors that may give a false designation. Such factors include wellbore effects, multi-phase flow, turbulent flow and other effects related to the well completion. Since the skin factor method is an indirect measure of formation damage, no "cause-effect" evaluation can be made from a pressure build-up test.

It is clear with the failings of the current formation damage evaluation systems that a new method for directly evaluating the type, severity, and extent of formation damage is needed.

SUMMARY OF THE INVENTION

The present invention is generally directed to a method for evaluating the type and extent of formation damage. The method of the present invention comprises taking core samples from the side of the wellbore in the zone of interest and evaluating those core samples to determine what, if any, formation damage exists. In a particularly preferred method of practicing the method of the present invention, core samples will be acquired through use of a rotary sidewall coring tool. Previously, sidewall coring has been utilized in formation logging and petrophysical evaluation of newly drilled wellbores. The acquired cores will be removed laterally from the wall of the wellbore. A number of different analyses may be run on the core samples to determine the type, severity and extent of formation damage. Cores may be taken from either cased or open wellbores utilizing the rotary sidewall coring tool.

DETAILED DESCRIPTION OF THE INVENTION

Figure 1:
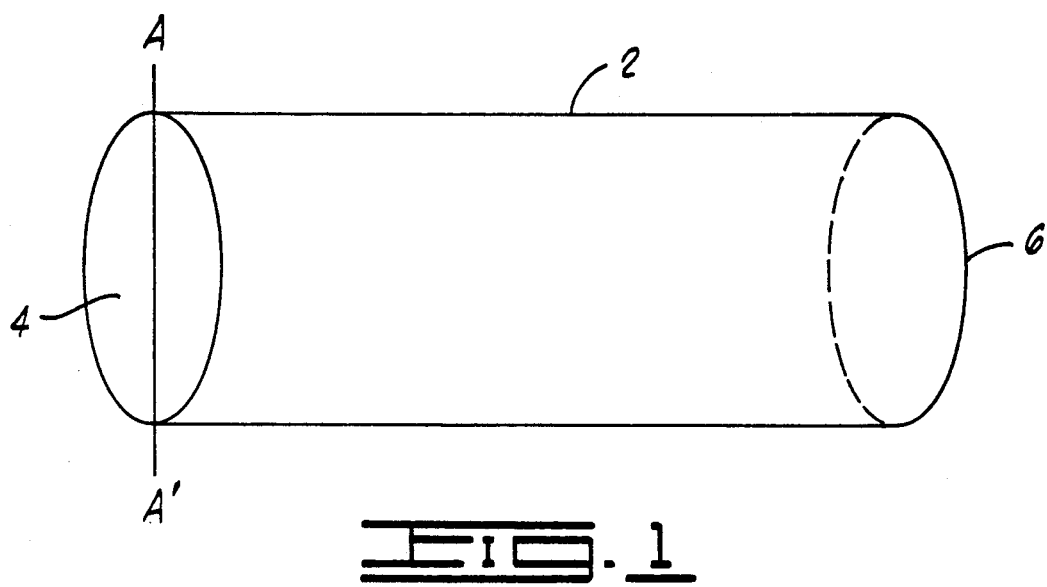
FIG. 1 is a schematic view of a formation core sample.

FIG. 1 illustrates a formation core sample 2 that is taken from the sidewall of a wellbore. The operator will clearly mark the end of the core which was from the wellbore face 4 and the end of the core which was out in the formation 6. The A—A' line delineates the orientation of the wellbore itself, usually vertical. In a preferred method the sidewall core is taken using a rotary sidewall coring tool. The core sample 2 after it is marked as described may then be tested using the various analysis methods discussed above. Core samples may be obtained in open-hole completions anytime during the life of the well, or before casing is set in a cased-hole wellbore. Cores may also be obtained by cutting through the casing. Such cores permit further evaluation of casing-cement formation bonding and any mud filter cake damage in the formation.

Figure 2:
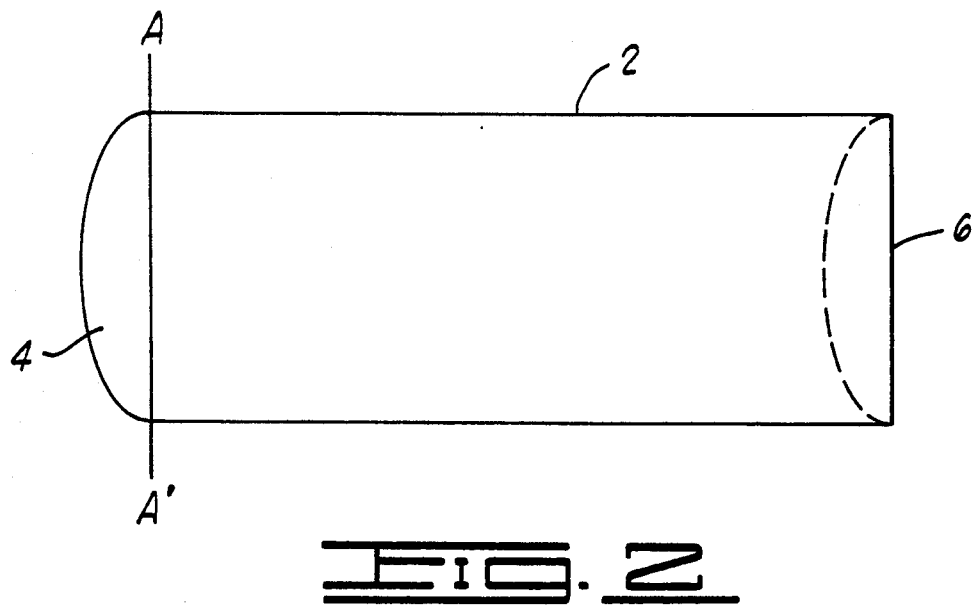
FIG. 2 is a schematic, cross-sectional view of the formation core sample of FIG. 1 cut along the A—A' line.

FIG. 2 illustrates the formation core sample 2 of FIG. 1 cut in half longitudinally along the A—A' line. This cross-section sample 2 allows a microscopic investigation of the interior of the core sample 2 so that the operator may determine the depth the damage extends into the formation. In addition, this will allow a microscopic investigation of the severity and the cause or type of formation damage.

When taking the core samples it is important to identify which end of the core sample was from the side of the wellbore and which end of the core sample extended out into the formation itself. From a general visual inspection of the core sample it can be determined if there is filter or mud cake damage on the surface of the core sample that made up part of the wellbore face. Visual inspection also readily identifies the ends of core samples removed from cased holes.

In using the present method a number of core samples may be taken so that some destructive analysis may be performed on the core samples. One type of analysis which may be used is a qualitative x-ray diffraction (XRD) analysis which can be done on a pulverized 1-gram sample of a core sample. The purpose of this analysis is to identify the types and relative quantities of minerals in the formation sample. The core can be segmented so that relative quantities of materials in each segment of the core beginning from the wellbore end and extending out into the formation can be analyzed showing the type, severity and extent of formation damage. The same x-ray diffraction (XRD) analysis may be used on any downhole scale found, any surface scale found, or other whole core samples as a method to compare and insure consistency of results of the XRD analysis.

Another analysis in the present invention which may be run on the core samples is a scanning electron microscope examination which provides a greatly magnified view of the core sample. This allows for identification of the minerals present and their locations. This test requires a core chip with a freshly broken surface which is coated with a gold palladium alloy and placed in a vacuum chamber of the SEM. An associated energy dispersive x-ray is used to help identify the mineral content of the sample. A photo micrograph can then be taken from which a pseudo-three-dimensional view of the formation pore spaces can be generated. This analysis allows the operator to determine what type of formation damage is occurring, how it is occurring, i.e., whether the formation rock is being coated or whether fines are accumulating in the pore spaces, where the formation damage is concentrated and how far it extends into the formation.

Other analyses that may be run include x-ray microanalysis elemental mapping, back-scattered electron microscopy, petrographic analysis, and optical microscopy. In addition, flow rate analyses may be performed on the core itself and compared against expected results using the known porosity and permeability of the reservoir. Further, chemicals could be used to treat the core itself in conjunction with the actual flow tests to determine if any improvement in the flow rate occurs after treatment.

The clearest advantage of the present invention over the prior art is the fact that all analysis is performed on the actual formation core samples. Therefore, the operator need not hypothesize or extrapolate what damage he or she believes extends into the formation. Specific scientific analysis can determine exactly what damage exists in the core samples and how far that damage extends into the formation. In addition, information about specifically how the damage is occurring, i.e., coating the rock, filling the pore space, causing a filter cake, etc., may be specifically determined so that the treatments may be designed to attack the specific problems. Further, the operator can quantify the extent of the damage so that the treatment need not be over or under-designed, either increasing the expense of the job or decreasing the efficiency of the job.

Another important advantage of the invention is the ability to analyze all damage that has occurred and not just damage that has occurred recently or that has occurred through rapid build-up. This advantage is specifically an improvement over the empirical method discussed above which looks for significant decreases in production or injection efficiency but does not take into account the gradual decline which may be accelerated by gradual damage build-up. For example, the present invention permits identification of gradual damage such as the formation of carbonate or sulfate scales within the pore spaces of the formation. Such information can provide a well operator with insight into the causes for cumulative production or injection rate declines over the life of a well and permit suitable remedial treatments to be effected. Thus, the present invention provides a method which could possibly reduce the rate of base decline in a producing well or increase base injection efficiency in an injection well. Thus, the present invention provides many advantages over the known methods of determining the extent of formation damage.

One exemplary environment in which the present invention may advantageously be utilized would be as in a producing well that has been producing for ten years and is now producing twenty percent of what it did ten years ago. The wellbore may be, by way of example, an open-hole completion with substantial footage of open hole.

After the production equipment is tripped out of the hole, the operator may run into the well with a rotary sidewall coring tool, to cut a plurality of sidewall cores. In addition to the core samples a scale sample if available should also be taken.

One of the cores may be segmented and pulverized. The powdered samples may be analyzed using X-ray diffraction to determine the types of minerals present in each segment of the original core sample. Using this analysis will allow the operator to determine where the damage exists in the core sample.

Some or all of the samples may be examined to determine the pore structure at the formation face. This can be done both visually and microscopically. In addition, surface material may be scraped from wellbore face of the core sample and that material may be analyzed.

A scanning electron microscope ("SEM") examination may also be performed on different segments of the core sample. The core segment or chip with a freshly broken surface is required for this examination. The sample is coated with a gold palladium alloy and placed in the vacuum chamber of the SEM. The core segment or chip is viewed at a high magnification and a photomicrograph is taken. An associated energy dispersive x-ray analysis ("EDX") is used to help identify the mineral content of the sample.

By using the SEM in conjunction with the energy dispersive x-ray, the framework grains of the sample can be identified and their size approximated. The location of the clay minerals within the sample can also be observed. The SEM can produce in effect a pseudo-three-dimensional view of formation pore spaces.

Using the SEM and associated energy dispersive x-ray the operator can first view portions of the surface of the core sample which was adjacent to the wellbore. The EDX analysis will identify minerals on the core's face.

The core can then be cut down its long axis, as illustrated in FIG. 2, and SEM and EDX analysis may be done in the same way on portions of the core sample moving down its axis toward the end of the core which extended into the formation. This process gives the operator a view of the pore structure throughout the core sample. Also it provides information concerning minerals that exist in the core sample and where those minerals exist in relation to the wellbore.

The SEM will also indicate whether the damage is the result of fines building up in the pore space or from minerals or other substances coating the framework grains. This information can greatly affect the treatment necessary to correct the problem. If the problem is simply fines building up in the pore space, and if those fines are not dissolvable by known treating methods, such as the use of hydrofluoric acid solutions to dissolve silicate materials, the best solution may be to fracture treat the well to extend beyond the damaged zone and open up more effective wellbore face. If the damage is merely an inch of acid soluble scale, spotting acid and allowing it to soak in may be the most effective and cheapest method of solving the damage problem. From these two examples, it is clear that the information gained from the SEM and other analysis may greatly affect the treatment selected.

The scale sample that was collected may be chemically analyzed to determine if the scale showing up in the wellbore is the same as exists in the formation. It is possible that an extra pressure drop is introduced by the production equipment design. That extra pressure drop may be enough to form paraffin or scale on the production equipment that does no form in the formation. If this is so, then the production equipment should be redesigned to eliminate the extra pressure drop. Once again, if only the scale sample were analyzed and a treatment designed from it, there would be no benefit to the formation, because it was not damaged, and the extra pressure drop in the production equipment would still not be corrected. However, the act of cleaning up the production equipment alone may temporarily improve production and give the operator a false sense of a job well done.

Finally, actual flow tests and chemical treatments may be performed on the cores. The actual results of the flow test are compared to expected results with the known reservoir permeability an porosity. This will indicate the severity of the damage. Treatments may then be performed on the cores and the flow test repeated until it is determined which treatment or combination of treatments will return the core to expected performance.

What is claimed is:

1. A method for diagnosing damage, comprising the steps of:
    obtaining a sidewall core sample from a subterranean formation penetrated by a wellbore;
    analyzing said formation core sample; and using said analysis to determine the type of scale damage, the severity of said damage, and the depth from the wellbore to which said damage extends.

2. The method of claim 1 wherein the step of obtaining said sidewall core sample is accomplished in part through use of a rotary sidewall coring tool.

3. The method of claim 1, wherein said step of analyzing said formation core sample comprises examining a partial sample obtained from said core with a scanning electron microscope.

4. The method of claim 1, wherein said step of analyzing said formation core sample comprises performing a qualitative x-ray diffraction (XRD) analysis.

5. The method of claim 1, wherein said step of analyzing said formation core sample comprises performing x-ray micro-analysis for elemental mapping of sample surface.

6. The method of claim 1, wherein said step of analyzing said formation core sample comprises performing back-scattered electron microscopy.

7. The method of claim 1, wherein said step of analyzing said formation core sample comprises performing petrographic analysis.

8. The method of claim 1, wherein said step of analyzing said formation core sample comprises performing optical microscopy.

9. The method of claim 1, wherein said step of analyzing said formation core sample comprises performing flow rate analyses.

10. A method for diagnosing formation damage, comprising the steps of:

taking a plurality of side-wall core samples from a subterranean formation penetrated by a wellbore;

analyzing said formation core samples; and using said analysis to determine parameters of the formation fines migration damage.

11. The method of claim 10 wherein said step of using said analysis comprises determining the severity of said formation damage, and the depth from the wellbore to which said formation damage extends.

12. The method of claim 10 wherein the step of obtaining said sidewall core sample is accomplished in part through use of a rotary sidewall coring tool.

13. The method of claim 10, wherein said step of analyzing said formation core sample comprises examining a partial sample obtained from said core with a scanning electron microscope.

14. The method of claim 10, wherein said step of analyzing said formation core sample comprises performing a qualitative x-ray diffraction (XRD) analysis.

15. The method of claim 10, wherein said step of analyzing said formation core sample comprises performing x-ray micro-analysis for elemental mapping of the sample surface.

16. The method of claim 10, wherein said step of analyzing said formation core sample comprises performing backscattered electron microscopy.

17. The method of claim 10, wherein said step of analyzing said formation core sample comprises performing petrographic analysis.

18. The method of claim 10, wherein said step of analyzing said formation core sample comprises performing optical microscopy.

19. The method of claim 10, wherein said step of analyzing said formation core sample comprises performing flow rate analyses.

* * * * *